United States Patent [19]

Falk et al.

[11] Patent Number: 4,568,250
[45] Date of Patent: Feb. 4, 1986

[54] LOW POWER ELECTROMAGNETIC PUMP

[75] Inventors: Theodore J. Falk, Clarence; Lawrence E. Morris, Bowmansville, both of N.Y.

[73] Assignee: Greatbatch Enterprises, Inc., Clarence, N.Y.

[21] Appl. No.: 496,822

[22] Filed: May 23, 1983

Related U.S. Application Data

[63] Continuation-in-part of Ser. No. 415,657, Sep. 7, 1982.

[51] Int. Cl.$^4$ .................. F04B 17/04; F04B 25/04
[52] U.S. Cl. ........................... 417/254; 417/417; 417/444; 417/487
[58] Field of Search .................. 417/417, 416, DIG. 1, 417/505, 486, 487, 444, 445, 244, 254, 257, 240, 241

[56] References Cited

U.S. PATENT DOCUMENTS

| | | | |
|---|---|---|---|
| 1,590,868 | 6/1926 | Wallace | 417/417 X |
| 1,690,348 | 11/1928 | Wallace | 417/417 |
| 2,634,805 | 4/1953 | Bills et al. | 417/417 |
| 3,601,509 | 8/1971 | Kreitchman | 417/417 |
| 4,152,098 | 5/1979 | Moody et al. | 417/413 |
| 4,274,407 | 6/1981 | Scarlett | 128/213 R |

FOREIGN PATENT DOCUMENTS 55-84880  6/1980  Japan .................. 417/DIG. 1

Primary Examiner—Cornelius J. Husar
Assistant Examiner—Peter M. Cuomo
Attorney, Agent, or Firm—Christel, Bean & Linihan

[57] ABSTRACT

An electromagnetic pump comprising a housing having a fluid receiving chamber in communication with an inlet, a pair of serially-connected fluid pumping chambers, one in communication with the fluid receiving chamber and the other in communication with an outlet, an electromagnet carried by the housing located external to the fluid chambers thereof, and a barrier in the form of a thin diaphragm of fluid impermeable material which heremetically isolates the electromagnet from the fluid chambers. An armature in the housing is movable within a body of magnetically permeable material, has a pole portion located for magnetic attraction by the electromagnet, and has first and second plunger portions in respective ones of the pumping chambers for forcing fluid out of the chambers and through the outlet. The armature is moved from a rest position through a forward pumping stroke when attracted by the electromagnet to force fluid from one pumping chamber to the other and then out of that chamber through the outlet, and the armature is moved by a biasing spring in an opposite direction through a return stroke back to the rest position. A pump check valve is within the pump and associated with the armature in the form of a valve member located in the fluid receiving chamber, movably carried by the armature, and positioned for closing the pump inlet when the armature is in the rest position and opening the inlet after the armature begins the forward pumping stroke. The arrangement is such that the volume of the fluid receiving chamber is minimized in the region between the check valve and the neighboring one of the armature plunger portions. Long term sealing against back flow is provided by a relatively stronger biasing spring, and short term sealing by a relatively weaker biasing spring.

16 Claims, 8 Drawing Figures

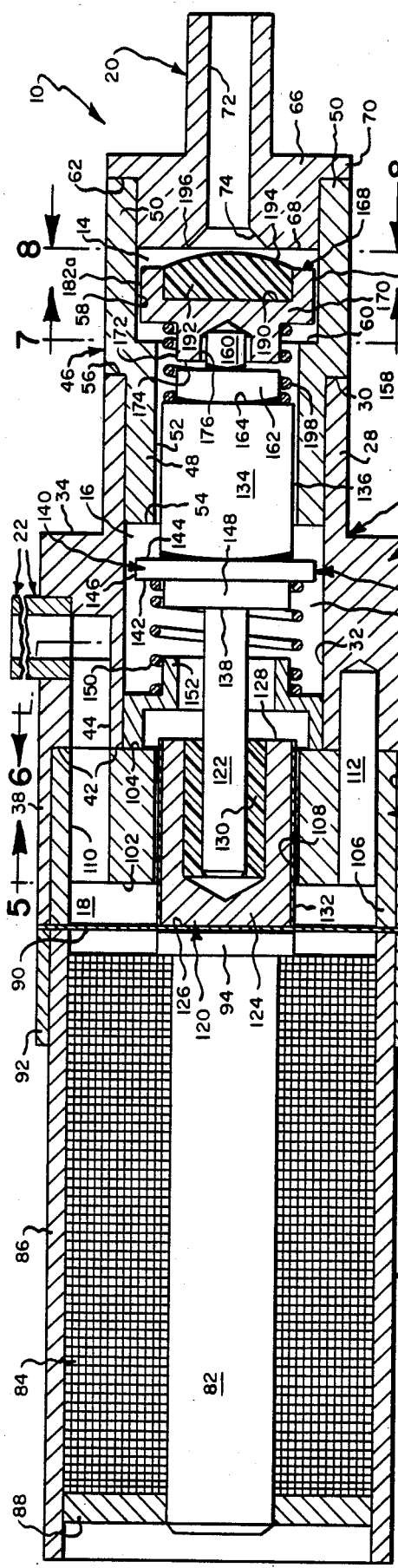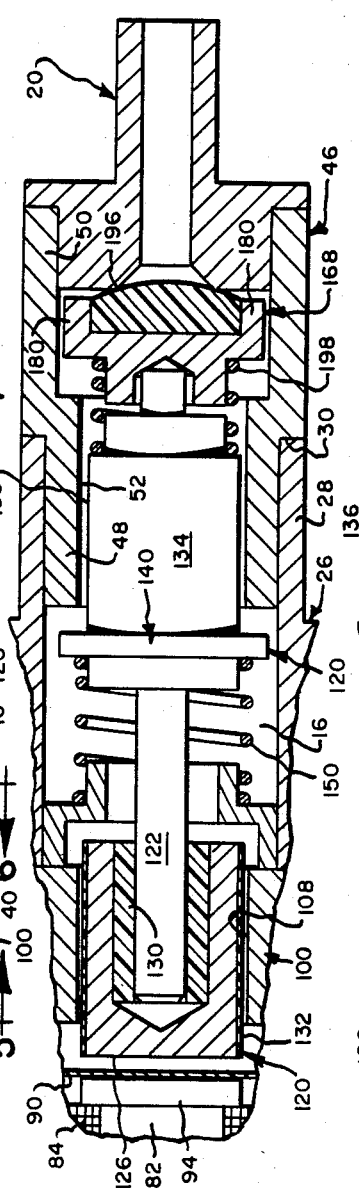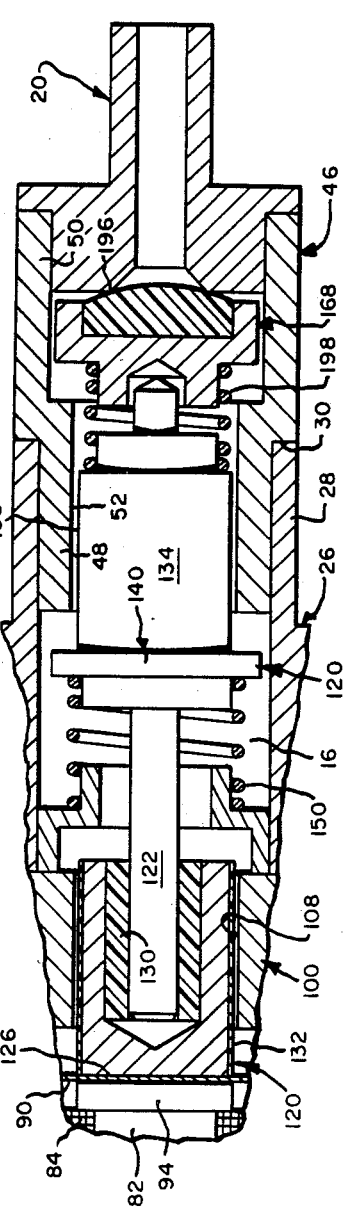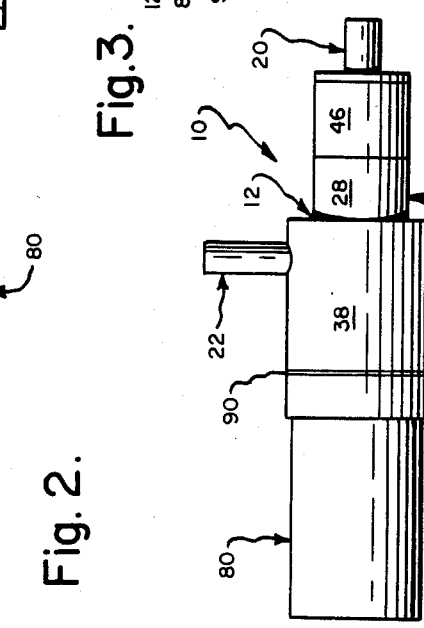

LOW POWER ELECTROMAGNETIC PUMP

CROSS REFERENCE TO A RELATED APPLICATION

This application is a continuation-in-part of our pending U.S. patent application Ser. No. 415,657 filed Sept. 7, 1982 and entitled "Low Power Electromagnet Pump".

BACKGROUND OF THE INVENTION

This invention relates to the art of electromagnetically-operated fluid pumps, and more particularly to a new and improved electromagnetic pump which operates at extremely low power.

One area of use of the present invention is implantable drug delivery systems, although the principles of the present invention can be variously applied. The principal requirements for a pump in such applications are low power drain, since the pump must be driven by an implanted battery, and compatibility with the drug being pumped. Other important requirements are that the pump be relatively insensitive to the presence of bubbles in the fluid being handled, be relatively easy to prime, and provide an adequate fluid pressure increase across the pump which is sufficient for the intended uses of the pump. A further requirement is to have low pressure drop across the pump check valve while at the same time providing satisfactory long term sealing against back flow.

It would, therefore, be highly desirable to provide an electromagnetically-operated pump which is safe, reliable, small in size, light in weight, which operates without excessive demand on the available energy supply, which is compatible with drugs or similar liquids to be pumped, which is relatively insensitive to the presence of bubbles in the fluid being pumped and relatively easy to prime, which provides an adequate fluid pressure increase across the pump sufficient for the uses intended, and which allows low pressure drop across the pump check valve while at the same time provides satisfactory long term sealing against back flow.

SUMMARY OF THE INVENTION

It is, therefore, a primary object of this invention to provide a new and improved electromagnetically-operated pump.

It is a more particular object of this invention to provide such a pump which operates at extremely low power levels.

It is a further object of this invention to provide such a pump which is compatible with drugs and similar liquids to be pumped.

It is a further object of this invention to provide such a pump which is electrically and magnetically efficient.

It is a further object of this invention to provide such a pump which is relatively insensitive to the presence of bubbles in the fluid being handled and relatively easy to prime.

It is a further object of this invention to provide such a pump which gives an adequate fluid pressure increase across the pump sufficient for the uses intended.

It is a further object of this invention to provide such a pump which allows low pressure drop across the pump check valve while at the same time provides satisfactory long term sealing against back flow.

It is a more particular object of this invention to provide such a pump which is small in size, light in weight and reliable in operation.

The present invention provides an electromagnetic pump comprising a housing having a fluid receiving chamber in communication with an inlet, a pair of serially-connected fluid pumping chambers, one in communication with the fluid receiving chamber and the other in communication with an outlet, electromagnet means carried by the housing located external to the fluid chambers thereof, and barrier means in the form of a thin diaphragm of fluid impermeable material which heremetically isolates the electromagnet from the fluid chambers. An armature in the housing is movable within a body of magnetically permeable material, has a pole portion located for magnetic attraction by the electromagnet and has first and second plunger portions in respective ones of the pumping chambers for forcing fluid out of the chambers and through the outlet. The armature is moved from a rest position through a forward pumping stroke when attracted by the electromagnet means to force fluid from one pumping chamber to the other and then out of that chamber through the outlet, and the armature is moved by biasing means in an opposite direction through a return stroke back to the rest position. A magnetic circuit is defined including the electromagnet means, a portion of the fluid-impermeable barrier, the body, the armature pole portion and a gap defined between the pole portion and the electromagnet which gap is closed during movement of the armature toward the electromagnet during energization thereof. The pump is made electrically and magnetically efficient by minimizing the total gap within the magnetic circuit, by having the pole face area relatively large on the armature pole portion, and by having the electromagnet include a coil on a core of relatively small diameter. A pump check valve is within the pump and associated with the armature in the form of a valve member located in the fluid receiving chamber, movably carried by the armature, and positioned for closing the pump inlet when the armature is in the rest position and opening the inlet after the armature begins the forward pumping stroke. The arrangement is such that the volume of the fluid receiving chamber is minimized in the region between the check valve and the neighboring one of the armature plunger portions. Long term sealing against back flow is provided by a relatively stronger biasing means, and short term sealing by a relatively weaker biasing means.

The foregoing and additional advantages and characterizing features of the present invention will become clearly apparent upon a reading of the ensuing detailed description together with the included drawing wherein:

BRIEF DESCRIPTION OF THE DRAWING FIGURES

FIG. 1 is a side elevational view of a pump according to the present invention;

FIG. 2 is an enlarged longitudinal sectional view of the pump of FIG. 1 showing the armature in an energized position and the check valve in an open position;

FIG. 3 is a fragmentary longitudinal sectional view of the pump of FIG. 2 showing the armature in a rest position;

FIG. 4 is a fragmentary longitudinal sectional view of the pump of FIG. 2 showing the armature in an energized position and the check valve in a closed position;

DETAILED DESCRIPTION OF THE ILLUSTRATED EMODIMENT

Figure 5:
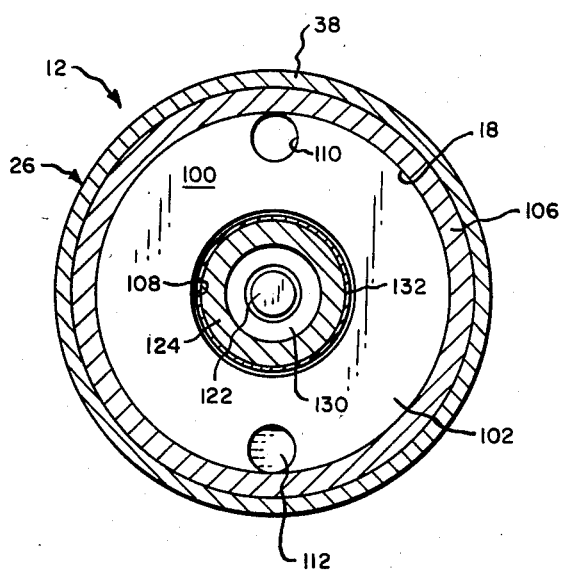
FIG. 5 is a sectional view taken about on line 5—5 in FIG. 2.
Figure 6:
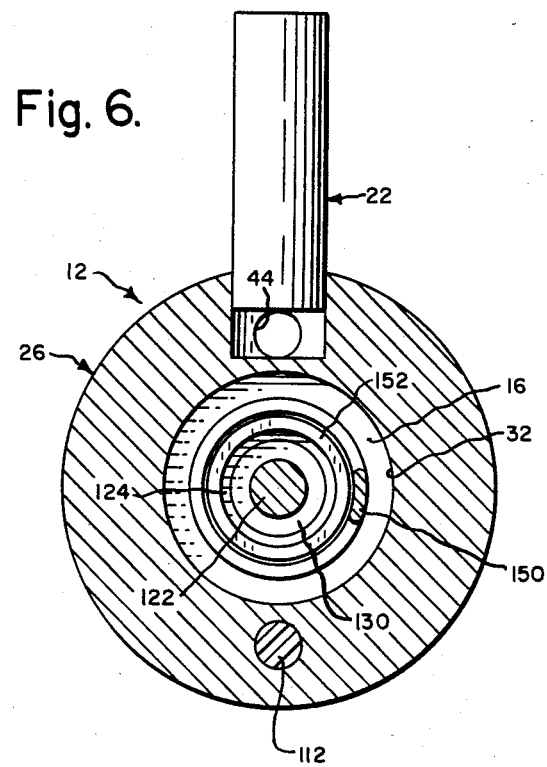
FIG. 6 is a sectional view taken about on line 6—6 in FIG. 2.

Referring now to FIGS. 1-4, a pump 10 according to the present invention includes a housing 12 which is generally hollow cylindrical in overall shape and includes an interior region for containing fluid, i.e. the liquid to be pumped. As shown in FIG. 2, the hollow interior region is divided in a manner which will be described into a fluid receiving chamber 14, a first fluid pumping chamber 16 in fluid communication with receiving chamber 14, and a second fluid pumping chamber 18 serially in fluid communication with pumping chamber 16. There is an inlet generally designated 20 in fluid communication with the receiving chamber 14 and adapted to be connected to a source or supply of fluid to be pumped. There is also an outlet 22 in fluid communication with the second pumping chamber and adapted to be in fluid communication with a location to which the fluid is to be pumped. There is provided check valve means operatively associated with the fluid containing region of pump 10 for allowing fluid flow in a direction from the inlet 20 through outlet 22 and blocking fluid flow in a direction from the outlet through the inlet. In the pump shown the check valve is within the pump and associated with the pump armature in a manner which will be described.

Referring now to FIG. 2, housing 12 is generally hollow cylindrical in overall shape including a main body portion 26 of relatively substantial wall thickness. Housing portion 26 has a first axial end section 28 extending from one end of housing portion 26, i.e. the right-hand end as viewed in FIG. 2, which is of relatively smaller wall thickness and terminates in an axial end face 30. Portion 26 and section 28 define an interior surface of constant diameter. Thus, the outer surface of housing portion 26 and section 28 are of different diameters and meet in an annular surface 34. The housing portion 26 has a second axial end section 38 extending from the other end of housing section 26, i.e. the left-hand end as viewed in FIG. 2, which also is of smaller wall thickness. End section 38 has a relatively larger diameter inner wall surface 40 which meets surface 32 in annular intermediate wall 42.

Main body portion 26 is provided with a longitudinal bore or passage 44 for placing the second pumping chamber 18 in fluid communication with outlet 22. Outlet 22 is located on the side of housing 12 for communication with the passage 44. Housing portion 28 is provided with a radially extending opening in the outer wall thereof in communication with passage 44.

A housing extension portion 46 is provided between main body portion 28 and inlet 20. Portion 46 is generally cylindrical having first and second axial sections 48 and 50, respectively. Section 48 is received snugly within housing section 28 with section 48 having an outer diameter substantially the same as the diameter of surface 32. Section 48 has an inner surface 52 and terminates in an axial end face 54 exposed to the first pumping chamber 16. Section 50 has an outer diameter substantially equal to the outer diameter of housing section 28 whereby the outer surfaces thereof are substantially flush. The outer surface of section 50 meets the smaller diameter outer surface of section 48 in an annular surface 56 which abuts end face 30. Section 50 has an inner surface 58 of a diameter larger than that of inner surface 52 of section 48, and the two inner surfaces 52,58 meet in an annular surface 60. Section 50 terminates in an axial end face 62.

Inlet 20 is provided by a plug-like element which is fitted into the open end of section 50 of the housing extension portion 46. The element includes a main body 66 generally cylindrical in shape and having an outer diameter substantially equal to the diameter of inner surface 58 of section 50 thereby providing a close fit therein. Body 66 has one axial end face 68 located in chamber 14, and adjacent the opposite end face the outer surface of body 66 is provided with an annular rim 70 which abuts the annular end face 62 for placement and securement of the fitting in the housing. The two components are secured together by welding or other suitable means. An internal bore 72 extends between the two opposite axial end faces of body 66 to provide an internal passage for the inlet. Passage 72 meets the inner axial end face 68 an annular, conical shaped surface 74. Inlet 20 is adapted for connection to a conduit such as a flexible tubing leading from a source or supply of fluid to be pumped.

By way of example, in an illustrative pump, housing 12 including main body portion 26 and extension portion 46, together with the inlet and outlet fittings 18 and 20, respectively, all are of metal, and for a drug delivery pump for implantation in a patient, titanium has been found to provide satisfactory results. In such an illustrative pump, housing 12 has an overall length of about 0.555 inch measured between the axial end faces of section 38 and 50. Surface 32 has a diameter of about 0.15 inch, and the axial end face 30 has a radial dimension of about 0.03 inch. Surface 40 has a diameter of about 0.26 inch, and the axial end face of housing section 38 has a radial thickness of about 0.02 inch. Passage 44 in housing body 26 and the interior passage in outlet fitting 22 both have a diameter of about 0.032 inch. Surface 52 has a diameter of about 0.100 inch, and axial end face 54 has a radial dimension of about 0.050 inch. Surface 58 has a diameter of about 0.135 inch, and axial end face 62 has a radial dimension of about 0.040 inch. The axial distance between end faces 54 and 62 is about 0.260 inch. In the inlet plug fitting 20, the passage 72 has a diameter of about 0.034 inch and surface 74 is disposed at an angle of about 45 degrees to the longitudinal axis of fitting 20.

The pump of the present invention further comprises electromagnet means generally designated 80 carried by housing 12 and located external to the fluid containing region of the housing. As shown in FIG. 2, the electromagnet 80 includes a core 82 in the form of a spool which is generally solid cylindrical in shape. A coil 84 is wound on spool 82 and contained within a hollow housing 86 generally cylindrical in shape. One end of electromagnet 80 is adjacent and in abutting relation to housing 12, and the opposite end, i.e. the left-hand end as viewed in FIG. 2, is closed by a plate element 88 fitted within the open end of housing 86 and fitted onto an end of spool 82. Electromagnet is joined to housing 12 in the following manner.

The interior, fluid containing region of housing 12 and the electromagnet 80 are separated by a barrier means of fluid impervious material in the form of a relatively thin plate or diaphragm-like component 90. The end of magnet housing 86 adjacent housing 12 is provided with an annular band 92 around the outer surface and adjacent the axial end face of housing 86. The outer diameter of band 92 when placed on housing 86 is substantially equal to the outer diameter of housing section 38 so that the respective outer surfaces are substantially flush.

The axial end faces of band 92 and magnet housing 86 are coplanar The housing and electromagnet structures are placed in abutting relation on opposite surface portions of the plate 90, and the assembly secured together by a weld joining the respective adjacent outer surfaces of band 92 and housing section 38. In addition, an enlarged annular end portion 94 of spool 82 contacts the central portion of plate 90 in a manner supporting the same.

By way of example, in an illustrative pump, spool 82, magnet housing 86 and closure 88 are of ferromagnetic material, for example 4750 nickel iron alloy. Plate 90 and band 92 are of titanium, the material of plate 90 being found suitable for use in the exemplary implanted drug delivery pump previously mentioned. Spool 82 has a length of about 0.555 inch and a diameter of 0.079 inch. Housing 86 has a wall thickness of about 0.03 inch, band 92 a thickness of about 0.02 inch and diaphragm 90 a thickness of about 0.001 inch. Coil 84 has about 3600 turns of 42 gauge wire.

The pump of the present invention further comprises a body 100 of magnetically permeable material in the fluid containing region of housing 12 and between the first and second fluid pumping chambers 16 and 18, respectively. In additon to providing separation between the two chambers, body 100 also defines a portion of the magnetic circuit in the pump, along with other components of the pump, in a manner which will be described. Body 100 is generally solid cylindrical in shape having an outer diameter substantially equal to the diameter of housing inner surface 40 of housing section 38 thereby providing a close fitting relationship. Body 100 has a main body portion between axial end surfaces 102 and 104 which is of an axial length less than the distance between housing surface 42 and plate 90 by an amount determined by the desired dimension of pumping chamber 18. Body 100 is formed to include an outer annular rim portion 106 extending from end face 102 and which abuts a corresponding surface portion of plate 90 as shown in FIG. 2. The radial thickness of rim portion 106 is substantially equal to that of magnet housing 86, and the two are in substantial alignment for maximizing transmission of magnetic flux therebetween in a manner which will be described. Body 100 is provided with a central through bore or passage 108 of substantial diameter for receiving a portion of the pump armature in a manner which will be described. The main portion of body 100 also is provided with a smaller through bore or passage 110 offset from passage 108 and of substantially the same diameter and in registry with outlet passage 44 thereby providing fluid communication between pumping chamber 18 and the outlet 22. Body 100 is positioned in housing 12 by means of a rod 112 extending through corresponding bores in body 100 and valve housing portion 26 shown in FIG. 2, the rod 112 preferably being of Teflon material and the parts being secured together by a compression fit.

By way of example, in an illustrative pump, body 100 is of mu-metal which is selected to provide the desired degree of magentic permeability while at the same time being compatible with medicine or the like for use in the exemplary implanted drug delivery pump previously mentioned. As is well known, mu metal includes nickel in a major portion with the balance including iron, copper and chromium. In addition, some or all of the external surfaces of body 100 can be plated or coated by palladium or other suitable material selected to enhance the compatibility of the drug with the external surface. The outer diameter of body 100 is about 0.26 inch, the axial length between end face 104 and the end face of rim 106 is about 0.130 inch, and the axial length between end faces 102,104 is about 0.1 inch. Passage 110 has a diameter of about 0.029 inch and the central passage 108 a diameter of about 0.1 inch.

The pump according to the present invention further comprises an armature generally designated 120 positioned in the fluid containing region of housing 12. The armature has a pole portion located for magnetic attraction by the electromagnet 80, a first plunger portion associated with the first pumping chamber 16 for forcing fluid from chamber 16 into chamber 18, and a second plunger portion associated with the second pumping chamber 18 for forcing fluid out of chamber 18 and outlet 22. The armature 120 is movably supported in housing 12 for movement from a rest position through a forward pumping stroke when attracted by the electromagnet 80 to force fluid out of the pumping chambers 16 and 18 through outlet 22, and for movement in an opposite direction through a return stroke back to the rest position. In FIG. 2, armature 120 is shown in a position at the end of the forward pumping stroke in response to energization of electromagnet 80, in FIG. 3 armature 120 is shown in the rest position at the end of the return stroke, and in FIG. 4 armature 120 is shown in an energized position and the check valve in a closed position which will be described in detail presently.

Armature 120 includes a shaft or rod portion 122 which is positioned in housing 12 with the longitudinal axis thereof generally coincident with the longitudinal axis of housing 12. Shaft portion 122 is of relatively small diameter. The armature further includes an enlarged body portion 124 of magnetically permeable material which provides the armature pole portion and the second plunger portion in a manner which will be described. Body 124 is solid cylindrical in shape having an outer diameter slightly smaller than the diameter of passage 108 in body 100. This is to allow reciprocal movement of armature body 124 within the body 100 during the forward and return strokes of armature 120. In addition, the sizes of the outer diameter of body 124 and the diameter of passage 108 are selected to provide a fluid leakage path from pumping chamber 18 to pumping chamber 18 to pumping chamber 16 during the armature return stroke in a manner which will be described. The armature body 124 terminates at the end facing electromagnet 80 in an axial end face 126 which serves as the pole face and is disposed substantially perpendicular to the armature axis. The pole face 126 together with electromagnet 80 define the magnetic circuit gap which is closed during the forward pumping stroke. The pole face 126 is of relatively large cross-sectional area as compared to the cross sectional area of the armature shaft portion 122. The body 124 also serves as one of the armature plunger portions because as the pole face 126 moves toward plate 90 during the forward stroke when magnet 86 is energized, body 124, upon moving into pumping chamber 18, displaces fluid therefrom forcing it out through passages 100,44 to outlet 22.

Shaft portion 122 is fixed to body 124 in the following manner. Body 124 is provided with a longitudinal bore extending inwardly from the opposite axial end face 128 which terminates within body 124 at a location spaced from pole face 126. A sleeve 130 or a suitable split bushing of fluoropolymer material such as Teflon is fitted in the bore, and the end of the armature shaft portion 122 is fixed in the sleeve or bushing 130. The foregoing is provided by a mechanical compression fit. In addition, the outer surface of body 124 is provided with a coating 132 of Teflon or like material for a purpose to be described.

Armature 120 includes another body portion 134 spaced axially from body 124, preferably integral with shaft portion 122, and of relatively larger diameter. Body portion 134 provides the armature first plunger portion in a manner which will be described. Body portion 134 has an outer surface 136 extending along a major portion of the axial length of body 134 and having an outer diameter slightly less than the diameter of inner surface 52 of housing section 48. This is to allow reciprocal movement of body portion 134 within housing section 48 during the forward and return strokes of armature 120. In addition, the sizes of the outer diameter of surface 136 and the inner diameter of surface 52 are selected to provide a fluid leakage path from pumping chamber 16 to receiving chamber 14 during the armature return stroke in a manner which will be described.

Body 134 terminates at the end facing body 124 in an annular end face 138 disposed substantially perpendicular to the armature axis and extending between the outer surface of body 134 and the shaft portion 122. Body 134 is formed to include an annular extension or flange 140 between surface 136 and end face 138, located a short axial distance from end face 138. Flange 140 includes opposite side faces 142,144 and an outer or peripheral face 146 spaced from housing inner surface 32. An annular outer surface 148 of body 134 and having a diameter slightly less than that of surface 136 is between flange 140 and end face 138. Surface 148 together with flange face 142 define an annular shoulder facing in an axial direction toward body 124 for a purpose to be described.

There is also provided first biasing means in the form of a coil spring 150 for urging armature 120 toward the rest position shown in FIG. 3. One end of spring 150 seats in the annular shoulder described above and defined by the flange 140 and body surface 148. The opposite end of spring 150 seats in an annular spring retainer element 152 which has an annular rim portion which abuts against the end face 104 of body 100 as shown in FIG. 2. The annular shape of retainer 152, with the two diameter rim sections, enables it to be located concentric with the armature shaft section 122 to receive the spring 150 which also is concentric with the shaft, while at the same time not interfering with body 124 during movement of the armature 120. The outer diameter of the largest rim portion of retainer 152 is substantially equal to the diameter of surface 32, and retainer 152 is merely located within the housing 12, being held in place by the force of spring 150.

Body 134 terminates at the end facing inlet 20 in an annular end face 158 disposed substantially perpendicular to the armature axis and meeting an axial extension 160 of relatively short axial length disposed toward inlet 20 and having a diameter approximately equal to the diameter of armature shaft portion 122. Extension 160 operatively engages the pump check valve in a manner which will be described. End face 158 terminates at the outer periphery thereof in an annular surface 162 of body 134 which has a diameter less than the diameter of surface 136 and which extends a relatively small distance axially inwardly from end face 158. Surface 162 terminates in an annular surface 164 disposed substantially perpendicular to the armature axis and which meets surface 136. Surfaces 162 and 164 define an annular shoulder facing inlet 20 for a purpose to be described.

By way of example, in an illustrative pump, the armature 120 including shaft portion 122 and body portion 134 is machined from metal, preferably titanium for use in the aforementioned illustrative implanted drug delivery pump. Armature body 124 is of mu-metal and retainer 152 is of titanium. In addition, the armature can be coated or plated with gold, or other suitable material, like body 100, chose to enhance the compatibility of the drug with the external surface. Also, the Teflon coating 132 on the outer surface of body 124 received in passage 108 serves to reduce friction. The combination of armature shaft portion 122 and body portion has an overall length of about 0.410 inch from the end fitted within body 124 to the outer end of the extension 160. The armature shaft portion 122 has a diameter of about 0.036 inch, surface 136 has a diameter of about 0.100 inch, surface 146 of flange 140 has a diameter of about 0.136 inch, surface 148 has a diameter of about 0.093 inch, extension 160 has a diameter of about 0.030 inch and surface 162 has a diameter of about 0.080 inch. From the outer end of extension 160, surfaces 158,164, and 144 are spaced axially therefrom distances of about 0.040 inch, 0.060 inch and 0.180 inch, respectively. Flange surface 146 has an axial width of about 0.015 inch and the distance between end face 138 and flange surface 144 is about 0.035 inch. Body 124 has an overall axial length of about 0.14 inch and an outer diameter of about 0.1 inch. Spring 150 is 0.005 titanium wire with the spring inner diameter being about 0.095 inch.

Figure 7:
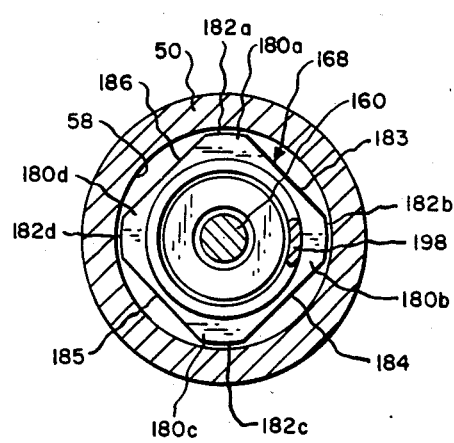
FIG. 7 is a sectional view taken about on line 7—7 in FIG. 2.
Figure 8:
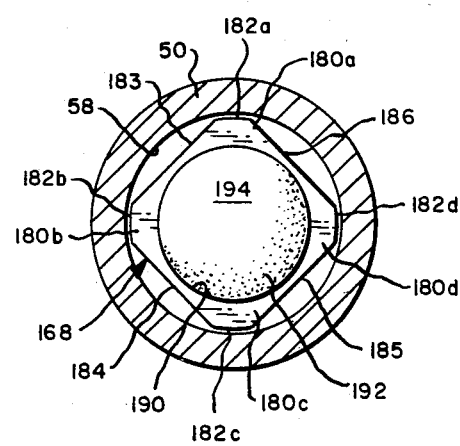
FIG. 8 is a sectional view taken about on line 8—8 in FIG. 2.

The pump according to the present invention further includes a check valve which is integral with the armature, i.e. the check valve is operatively coupled to the armature and is located in the fluid-receiving region of the housing for opening and closing the pump inlet. In particular, the check valve comprises a valve member movably carried by the armature and positioned for closing the pump inlet when the armature is in the rest position and for opening the inlet after the armature begins movement associated with the forward pumping stroke. As shown in FIGS. 2-4, the check valve, generally designated 168, is located in fluid receiving chamber 14 between inlet 20 and the end of armature 120 and includes a main body portion 170 generally cylindrical in shape having an outer surface 172 spaced radially inwardly from housing surfaces 52,58. Surface 172 has a diameter substantially the same as that of surface 162 of body 134. Body portion 170 terminates at the end facing armature 120 in an axial end face 174 disposed substantially perpendicular to the longitudinal axis of armature 120. An axially inwardly extending recess in the form of bore 176 is provided in surface 174 coaxial with the longitudinal axis of armature 120 and extending along within check valve body 170. Recess 176 receives extension 160 of armature body 134. The check valve body 170 is formed to include a plurality, in the present illustration four, radially extending formations or lands 180a–180d as shown also in FIGS. 7 and 8. Each land formation 180a–180d has a relatively short, curved outer edge 182a–182d, respectively, close to the inner surface 58 of housing section 50 for guiding the check valve 168 as chamber 14. Each land is separated from an adjacent land by a corresponding straight edge 183, 184, 185 and 186 as shown in FIGS. 7 and 8 thereby providing a flow space of significant area between the particular straight edge and the corresponding curved portion of surface 58. The lands 180a–180d also define a plurality of shoulders facing in an axial direction toward armature 120 for a purpose to be described.

The end face of body 170 facing inlet 20 is provided with a recess 190 to receive a disc-shaped valve element 192 having a smooth, convex outer surface 194 facing inlet 20. In particular, surfaces 74 and 68 of inlet fitting 20 meet in a sharp, annular valve seat edge 196 which is contacted in seating contact or engagement by surface 194 of valve element 192. Edge 196 is of a diameter larger than the diameter of inlet passage 72. There is provided second biasing means for urging check valve 168 into a position closing inlet 20. In particular, valve element surface 194 is biased into seating contact with edge 196 by the second biasing means acting on check valve 168 in the form of coil spring 198. One end of spring 198, i.e. the left-hand end as viewed in FIGS. 2–4, is seated in the shoulder provided by lands 180 on check valve body 170, and the opposite end of spring 198 is seated in the annular shoulder defined by surfaces 162 and 164 of armature body 134.

By way of example, in an illustrative pump, check valve body 170 is of titanium and has an overall axial length of about 0.070 inch. Surface 172 of valve body 170 has a diameter of about 0.080 inch and bore 176 has a diameter of about 0.030 inch and an axial length of about 0.030 inch. Each of the land portions 180a–180d has an axial length of about 0.040 inch, each edge 182a–182d has a length of about 0.020 inch and edges 182a–182d lie about on a circle having a diameter of about 0.130 inch. Recess 190 has a diameter of about 0.100 inch and an axial length of about 0.025 inch. Valve element 192 is of Dow Corning Silastic material MDX4-4210 which is heat curved in place into recess 192. Surface 74 of inlet fitting 20 defines an angle of about 45 degrees with the housing longitudinal axis. Spring 198 is 0.005 diameter titanium wire with the spring inner diameter being about 0.182 inch.

In operation, inlet 20 is connected to a source or supply of fluid to be pumped, and outlet 22 is connected to a point or location of use for the pumped fluid. The armature 120 is moved through a forward pumping stroke in response to electrical energization of electromagnet 80. One way of energizing magnet 80 is to charge a capacitor from a battery and then discharge that capacitor through coil 84. Other procedures can of course be employed for electrically energizing coil 84 in a known manner. Prior to electrical energization of magnet 80, armature 120 is in the rest position illustrated in FIG. 3 where the check valve 168 is located with convex surface 194 seated against edge 196 surrounding the opening of passage 72 to block fluid communication from inlet 20 to the fluid receiving chamber 14. In the rest position of armature 120, pole face 126 is spaced from diaphragm 90 as shown in FIG. 3 thereby defining the gap in the magnetic circuit. In the rest position this gap between pole face 126 and diaphragm 90 is of maximum length.

When coil 84 is electrically energized, the armature pole portion 124 is attracted toward magnet 80 thereby causing armature 120 to be drawn toward diamphragm 90. Electromagnetic flux travels through the magnetic circuit including the electromagnet core 82, plate 88, magnet housing 86, rim 106 of body 100, the included portion of diaphragm 90 between housing 86 and rim 100, body 100, armature pole portion 124, and the gap between pole face 126 and diaphragm 90. As armature 120 is moved in the forward pumping stroke, i.e. in a direction to the left as viewed in FIGS. 2–4, fluid initially contained in the first pumping chamber 16 i.e. the region within housing inner surface 32 and between end face 54 of housing section 48 and face 104 of body 100, is forced by armature body portion 134, particularly end face 138 and flange 140 thereof, through the gap or clearance between armature pole portion 124 and passage 108 in body 100 into the second pumping chamber 18. Simultaneously, fluid contained in the second pumping chamber 18, i.e. the region between body 100, diaphragm 90 and pole portion 124, is thereby forced through passages 110 and 44 and out through the outlet 22. The clearance between outer surface 136 of body armature portion 134 and the inner surface 52 of housing section 48 is selected to be sufficiently small so that fluid leakage therebetween is relatively small during the forward pumping stroke of armature 120.

The check valve 168 slides freely with respect to the armature 120 and does not necessarily move when the armature 120 is drawn toward diaphragm 90. Such relative positions are illustrated, for example, in FIG. 4. At rest, the surface 194 of check valve element 192 is held in contact with the valve seat defined by edge 196 by the spring 150 acting upon the armature 120 which is then in contact with the check valve body 170 as shown in FIG. 3. When the armature 120 is drawn toward diaphragm 90, the force of spring 150 is no longer transferred to the check valve 168 and the force holding the valve surface 194 against the valve seat is decreased to that provided by spring 198, which generally provides a force less than that provided by spring 150. If armature 120 is drawn toward electromagnet 80, with sufficient velocity, pressure within the pump housing 12 between the end of armature body 134 and housing surface 60 and the check valve seat decreases to a level below the level at the pump inlet 20 and the net force due to fluid pressure from inlet 20 acting on the check valve 168 tends to move the check valve surface 194 away from the seat provided by edge 196. If the net force due to the fluid pressure exceeds that applied by the spring 198, then check valve 168 moves away from the valve seat and fluid flows into the pump body as illustrated in FIG. 2. In fact, because the fluid is nearly incompressible the check valve 168 opens at approximately the same time that the armature 120 achieves enough velocity to force fluid out of the pump outlet 22. The forward pumping stroke of the armature 120 is completed when the pole face 126 approaches contact with the diaphragm 90. Actual contact may not be achieved since viscosity limits outflow of the fluid between the pole face 126 and the diaphragm 90. When the armature velocity decreases to a level such that the displacement rate of the motion of the pole portion 124, no longer exceeds the leak rate between the outer surface 136 of armature body portion 134 and inner surface of housing section 48, the pressure within the pump housing 12 begins to increase. When the force due to the pressure difference across the check valve 168 no longer exceeds the force of spring 198, the check valve member moves toward the valve seat and prevents flow out of the inlet port 20 of the pump as illustrated, for example, in FIG. 4.

When electrical excitation of coil 84 ceases, armature 120 is moved in the opposite direction, i.e. to the right as viewed in FIGS. 2–4, by the force of biasing spring 150 until the armature reaches the rest position as shown in FIG. 3 with surface 194 seated on edge 196 surrounding the opening of passage 72. This motion is relatively slow since it is limited by the small leak rate of fluid between the outer surface 136 of armature body portion 134 and the inner surface 52 of housing section 48 at a pressure difference determined by the force applied by the spring 150. During the return stroke of armature 120 the check valve 168 is held against the valve seat primarily by the light spring 198 supplemented by the difference between the outlet and inlet pressures acting on the valve seat. When the return stroke has been completed the spring force is increased to that of spring 150. Thus, the average pumping rate which is determined by the rate of return of armature 120 to the rest position can be relatively slow, but such a pumping rate is called for in typical implantable drug delivery systems. Armature 120 then remains in the rest position of FIG. 3 with inlet 20 closed and waiting for the next forward pumping stroke which occurs when magnet 80 is energized again.

Long term sealing is provided by the relatively stronger spring 150, and short term sealing while the armature 120 is forward is provided by the relatively weaker spring 198. As a result, there can be satisfactory sealing against the back flow when the pump is not in operation, while the pressure drop across the check valve 168 during the pump stroke is small.

The provision of armature portion 134 and the housing sections 48,50 at the inlet end of pump 10 results in a major decrease in the internal volume between the pump piston or armature 120 and the pump check valve 168. This reduction has the effect of making the pump less sensitive to the possible presence of a bubble in the fluid within the pump. As a result, the pump 10 is much easier to prime, and the use of carbon dioxide is normally not required for this purpose. When a bubble is introduced into the pump 10 along with the fluid stream, the flow rate decreases temporarily but recovers to its normal level as the bubble dissolves in the fluid. In addition, the volume per stroke of pump 10 is relatively less sensitive to back pressure.

The gap or clearance between armature pole portion 124 and passage 108 is relatively less critical to the extent that pump 10 relies on armature plunger portion 134 in addition to plunger portion 124 to provide the pressure increase. The Teflon coating 132 on the pole button or body 125 avoids high side forces on the pole button and the resulting drag as the pole button is pulled in a direction toward the armature spindle or shaft portion 122. The use of the Teflon coating 132, which is soft and somewhat uneven, makes it difficult to maintain a small clearance between the pole button 134 and the solenoid ring or body 100. In pump 10 greater clearance is allowable between these two parts. The requirement for close tolerance is shifted to two titanium parts which may not need to be coated, i.e. the armature portion 134 and the housing section 48.

The arrangement of armature plunger portions 134 and 124 in pumping chambers 16 and 18, respectively, provides two pumping elements in series. A higher pressure increase across pump 10 would appear to be possible and a bubble in one of the pumping chambers would affect one but not both pumping elements.

Thus, pump 10 of the present invention has the advantage of being relatively insensitive to the presence of bubbles in the fluid being handled, being relatively easy to prime, and providing an adequate fluid pressure increase across the pump. sufficient for the uses intended. Pump 10 also has the advantage of operating at extremely low power levels, being compatible with drugs and similar liquids to be pumped, being electrically and magnetically efficient, and being small in size, light in weight and reliable in operation. In particular, the non-movable diaphragm 90 of titanium or like material provides an hermetic seal between the fluid in housing 12 and the electrical components associated with magnet 80. Having armature 120 immersed in the fluid makes operation of the pump nearly independent of ambient pressure. The initial condition of the pump when armature 120 is in the rest position of FIG. 3 is that the fluid is at substantially the same pressure on opposite sides of the pump piston, i.e. in the receiving chamber 14 and in the pumping chambers 16 and 18.

The pump of the present invention is made electrically and magnetically efficient by minimizing the total gap within the magnetic circuit, by having the magnetic pole face 126 of relatively large surface area, and by having core 82 of relatively small diameter. In particular, there is a relatively large contact area at the interface between the axial end face of magnet housing 86 and diaphragm 90 and between diaphragm 90 and the axial end face of rim 106 of body 100 to minimize the effective air gap introduced by diaphragm 90 at this point in the magnetic circuit. Related to this is the need for welding diaphragm 90 to the band 92 and housing section 38 to achieve an hermetic seal between electromagnet 80 and the fluid containing region of housing 12 while at the same time not adversely affecting the magnetic circuit. In addition, there is a relatively large surface area along the gap between body 100 and pole portion 124 to minimize the effective air gap introduced at this point in the magnetic circuit. The relatively small diameter of core 82 provides the necessary ampere turns with a mimimum electrical resistance. The large area of pole face 126 provides a high magnetic force with a mimimum number of ampere turns. Having the magnetic gap external to coil 84, i.e. between pole face 126 and diaphragm 90, allows the foregoing features to be achieved simultaneously.

It is therefore apparent that the present invention accomplishes its intended objects. While an embodiment of the present invention has been described in detail, this is for the purpose of illustration, not limitation.

We claim:

1. An electromagnetic pump comprising:
(a) an elongated housing having a longitudinal axis and having an interior fluid containing region including a fluid receiving chamber, a first fluid pumping chamber in fluid communication therewith, a second fluid pumping chamber in fluid communication with said first pumping chamber, an inlet in fluid communication with said receiving chamber and an outlet in fluid communication with said second pumping chamber;
(b) electromagnet means carried by said housing and located external to said fluid containing region;

(c) an armature positioned in said fluid containing region of said housing for movement along said housing longitudinal axis and having a pole portion located for magnetic attraction by said electromagnet means and having a first plunger portion in said first pumping chamber for forcing fluid out of said first chamber into said second chamber and a second plunger portion in said second pumping chamber for forcing fluid out of said second chamber through said outlet; said armature being movably supported in said housing for movement from a rest position through a forward pumping stroke when attracted by said electromagnet means to force fluid from said pumping chambers through said outlet and for movement in an opposite direction through a return stroke back to said rest position;

(d) means for defining a magnetic circuit including said electromagnet means and said armature and a gap between said pole portion of said armature and said electromagnet means for moving said armature toward said electromagnet means to close said gap in response to electrical energization of said electromagnet means;

(e) check valve means operatively coupled to said armature and located in said fluid receiving chamber of said housing for closing said inlet when said armature is in said rest position and for opening said inlet after said armature begins movement associated with said forward pumping stroke, said check valve means allowing fluid flow in a direction from said inlet through said outlet and blocking fluid flow in a direction from said outlet through said inlet;

(f) said second armature plunger portion having a pole face disposed in a plane substantially perpendicular to the direction of movement of said armature, said pole face being located to define said gap with said electromagnet means, said pole face being of relatively large area; and (g) said fluid-containing region of said housing and said electromagnetic means being in axially spaced relation along said housing longitudinal axis and being separated by barrier means of fluid impervious material.

2. A pump according to claim 1, wherein said check valve means is in relatively close-fitting relation to the portion of said housing defining said fluid receiving chamber, said check valve means is closely coupled to and located closely adjacent said armature, and the portion of said armature adjacent said check valve means is in relatively close-fitting relation to said housing thereby decreasing the volume of said interior fluid containing region between said armature and said check valve means.

3. A pump according to claim 2, wherein the cross-sectional dimension of said armature portion adjacent said check valve means and the cross-sectional size of the associated portion of said housing are so related to define a close tolerance space therebetween serving as a leakage path for fluid from said first pumping chamber to said receiving chamber during movement of said armature through said return stroke.

4. A pump according to claim 1, wherein said housing includes a cylindrical portion adjacent said inlet and having a first inner diameter section containing said check valve means in relatively close-fitting relation and a second, smaller inner diameter section containing said first plunger portion of said armature in relatively close-fitting relation, said check valve means being closely coupled to and located closely adjacent said armature, thereby decreasing the volume of said interior fluid containing region between said armature and said check valve means.

5. A pump according to claim 4, wherein the inner diameter of said second housing section and the outer diameter of said armature first plunger portion are so related to define a close tolerance space therebetween serving as a leakage path for fluid from said first pumping chamber to said receiving chamber during movement of said armature return stroke.

6. A pump according to claim 1, further including a body of magnetically permeable material in said housing fluid containing region between said first and second fluid pumping chambers, said body defining a portion of said magnetic circuit, said body having a passage therethrough for receiving said second armature plunger portion in a movable, relatively close-fitting relation whereby said armature moves in said body during said forward and return strokes and said magnetic circuit is through said body and said second armature plunger portion.

7. A pump according to claim 6, further including a protective coating on the outer surface of said second armature plunger portion which moves in said passage.

8. A pump according to claim 7, wherein said protective coating is of fluoropolymer material.

9. A pump according to claim 1, further including biasing means in said housing for urging said armature toward said rest position.

10. A pump according to claim 1, further including:
(a) first biasing means for urging said armature toward said rest position;
(b) second biasing means for urging said check valve means toward a position closing said inlet; and
(c) the force provided by said first biasing means being greater than the force provided by said second biasing means.

11. A pump according to claim 1, wherein said inlet is located at one end of said housing, and said check valve means is located at one end of said armature disposed toward said inlet.

12. A pump according to claim 11, wherein said inlet comprises a passage terminating in an annular valve seat facing said check valve means and wherein said check valve means has a surface moved into and out of contact with said valve seat for closing and opening said inlet.

13. A pump according to claim 1, further including
(a) first biasing means operatively associated with said armature for providing long term sealing of said pump inlet;
(b) second biasing means operatively associated with said check valve means for providing short term sealing of said pump inlet; and
(c) the force provided by said second biasing means being weaker than the force provided by said first biasing means;
(d) whereby sealing against back flow is provided when said pump is not in operation while pressure drop across said check valve means is relatively small during the pumping stroke.

14. A pump according to claim 1, wherein said barrier means is disposed in a plane substantially perpendicular to said housing longitudinal axis.

15. An electromagnetic pump comprising:
(a) a housing having an interior fluid containing region including a fluid receiving chamber, a first fluid pumping chamber in fluid communication therewith, a second fluid pumping chamber in fluid communication with said first pumping chamber, an inlet in fluid communication with said receiving chamber and an outlet in fluid communication with said second pumping chamber;

(b) electromagnet means carried by said housing and located external to said fluid containing region;

(c) an armature positioned in said fluid containing region of said housing having a pole portion located for magnetic attraction by said electromagnet means and having a first plunger portion in said first pumping chamber for forcing fluid out of said first chamber into said second chamber and a second plunger portion in said second pumping chamber for forcing fluid out of said second chamber through said outlet; said armature being movably supported in said housing for movement from a rest position through a forward pumping stroke when attracted by said electromagnet means to force fluid from said pumping chambers through said outlet and for movement in an opposite direction through a return stroke back to said rest position;

(d) means for defining a magnetic circuit including said electromagnet means and said armature and a gap between said pole portion of said armature and said electromagnet means for moving said armature toward said electromagnet means to close said gap in response to electrical energization of said electromagnet means;

(e) check valve means operatively coupled to said armature and located in said fluid receiving chamber of said housing for closing said inlet when said armature is in said rest position and for opening said inlet after said armature begins movement associated with said forward pumping stroke, said check valve means allowing fluid flow in a direction from said inlet through said outlet and blocking fluid flow in a direction from said outlet through said inlet;

(f) said check valve means being in relatively close-fitting relation to the portion of said housing defining said fluid receiving chamber, said check valve means being closely coupled to and located closely adjacent said armature, and the portion of said armature adjacent said check valve means being in relatively close-fitting relation to said housing thereby decreasing the volume of said interior fluid containing region between said armature and said check valve means;

(g) first biasing means operatively engaging said first plunger portion of said armature for urging said armature toward said rest position and providing long term sealing of said pump inlet;

(h) second biasing means operatively engaging said first plunger portion of said armature and said check valve means for urging said check valve means toward a position closing said inlet and providing short term sealing of said pump inlet;

(i) the force of said first biasing means being transferred to said check valve means when said armature is in said rest position; and (j) the force provided by said second biasing means being weaker than the force provided by said first biasing means;

(k) whereby sealing against back flow is provided when said pump is not in operation while pressure drop across said check valve means is relatively small during the pumping stroke.

16. A pump according to claim 15, wherein the cross-sectional dimension of said armature portion adjacent said check valve means and the cross-sectional size of the associated portion of said housing are so related to define a close tolerance space therebetween serving as a leakage path for fluid from said first pumping chamber to said receiving chamber during movement of said armature through said return stroke.

* * * * *